(12) United States Patent
Xiao et al.

(10) Patent No.: US 11,085,059 B2
(45) Date of Patent: Aug. 10, 2021

(54) METHYLOPILA SP. AND USE THEREOF IN SELECTIVE RESOLUTION PREPARATION OF (S)-α-ETHYL-2-OXO-1-PYRROLIDINEACETATE

(71) Applicant: CHANGXING PHARMACEUTICAL CO. LTD., Zhejiang (CN)

(72) Inventors: Yanming Xiao, Zhejiang (CN); Likun Zhang, Zhejiang (CN); Minfan Qian, Zhejiang (CN); Yanbing Yan, Zhejiang (CN); Weiping Tan, Zhejiang (CN)

(73) Assignee: CHANGXING PHARMACEUTICAL CO. LTD., Zhejiang (CN)

( * ) Notice: Subject to any disclaimer, the term of this patent is extended or adjusted under 35 U.S.C. 154(b) by 0 days.

(21) Appl. No.: 16/466,171

(22) PCT Filed: Sep. 19, 2017

(86) PCT No.: PCT/CN2017/102275
§ 371 (c)(1),
(2) Date: Jun. 3, 2019

(87) PCT Pub. No.: WO2018/103409
PCT Pub. Date: Jun. 14, 2018

(65) Prior Publication Data
US 2019/0360011 A1    Nov. 28, 2019

(30) Foreign Application Priority Data

Dec. 5, 2016   (CN) .......................... 201611106084.2

(51) Int. Cl.
| | |
|---|---|
| *C12P 17/10* | (2006.01) |
| *C12N 11/14* | (2006.01) |
| *C12R 1/01* | (2006.01) |
| *C12P 41/00* | (2006.01) |

(52) U.S. Cl.
CPC .............. *C12P 17/10* (2013.01); *C12N 11/14* (2013.01); *C12R 1/01* (2013.01); *C12P 41/005* (2013.01)

(58) Field of Classification Search
CPC ...................................................... C12P 41/001
See application file for complete search history.

(56) References Cited

FOREIGN PATENT DOCUMENTS

CN          106591179         4/2017

OTHER PUBLICATIONS

Written Opinion and International Search Report of PCT/CN2017/102275 dated Dec. 6, 2017, 14 pages (English and Chinese).

*Primary Examiner* — Bin Shen
(74) *Attorney, Agent, or Firm* — Rankin, Hill & Clark LLP

(57) ABSTRACT

*Methylopila* sp. and use thereof in the selective resolution preparation of (S)-α-ethyl-2-oxo-1-pyrrolidineacetate. *Methylopila* sp. that produces enzymes is subjected to cell immobilization, and is then applied to the biological resolution of a racemate (R,S)-α-ethyl-2-oxo-1-pyrrolidineacetic acid ethyl ester to prepare high optically pure (S)-α-ethyl-2-oxo-1-pyrrolidineacetic acid ethyl ester, which is further subjected to a hydrolysis reaction to obtain (S)-α-ethyl-2-oxo-1-pyrrolidineacetate. The present invention achieves a high conversion yield up to 50.0% or more, a good stereoselectivity, and an enantiomeric excess value e.e.$_s$ (%) of (S)-α-ethyl-2-oxo-1-pyrrolidineacetic acid ethyl ester not less than 99.5; the catalytic efficiency is high; the concentration of the racemic substrate in the resolution reaction is up to 500 g/L, the reaction time does not exceed 15 h, the number of reuse times of the immobilized cells is not lower than 35.

13 Claims, 3 Drawing Sheets
Specification includes a Sequence Listing.

SEQUENCE LISTING

<160> NUMBER OF SEQ ID NOS: 1

<210> SEQ ID NO 1
<211> LENGTH: 1411
<212> TYPE: DNA
<213> ORGANISM: Methylopila sp.

<400> SEQUENCE: 1

```
acttccccca gtcgctgacc ctaccgtggt cgcctgcctc ccttgcgggt tagcgcagcg      60
ccttcgggta aaaccaactc ccatggtgtg acgggcggtg tgtacaaggc ccggaacgt      120 attcaccgcg gcatgctgat ccgcgattac tagcgattcc aacttcatgc actcgagttg     180
cagagtgcaa tccgaactga dacggctttt ggagattagc tccgggtcac cccttcgctg     240
cccactgtca ccgccattgt agcacgtgtg tagcccagcc cgtaagggcc atgaggactt     300
gacgtcatcc ccaccttcct cgcggcttat caccggcagt cccctagag tgcccaacca     360 aatgctggca actaggggcg agggttgcgc tcgttgcggg acttaaccca acatctcacg     420
acacgagctg acgacagcca tgcagcacct gtctctgtgt ccccgaaggg aaccccaaat     480
ctctctggat gtcacaggat gtcaaaggct ggtaaggttc tgcgcgttgc ttcgaattaa     540
accacatgct ccaccgcttg tgcgggcccc cgtcaattcc tttgagtttt aatcttgcga     600
ccgtactccc ccaggcggga cgcttaaagc gttagctgcg ccactgacca gcatgctggc     660
caacggctag cgtccatcgt ttacggcgtg gactatcagg gtatctaatc ctgtttgctc     720
cccacgcttt cgcacctcag cgtcagtatc gggccagtga gccgcttcg ccactggtgt      780 tcttgcgaat atctacgaat ttcacctcta cactcgcagt tccactcacc tctcccgaac     840
tcaagacttc cagtatcaag ggcagttcca aggttgagcc ttgggatttc accctgact      900 taaaagtccg cctacgtgcg ctttacgccc agtgattccg aacaacgcta gcccccttcg     960
tattaccgcg gctgctggca cgaagttagc cggggcttct tctctgggta ccgtcattat    1020
cttccccagt gaaagagctt tacaacccta aggccttcat cactcacgcg gcatggctgg    1080
atcaggcttg cgcccattgt ccaatattcc ccactgctgc ctcccgtagg agtctgggcc    1140
gtgtctcagt cccagtgtgg ctgatcatcc tctcagacca gctatggatc gtcgccttgg    1200
tgagccgtta cctcaccaac tagctaatcc aacgcgggtt gatctggtgg cgataaatct    1260
ttccccaaaa gggcttatac ggtattagct caagtttccc tgagttgttc cgtaccacca    1320
ggcacatccc cacgcgttac tcacccgtct gccgctcacc ccgagggatg cgctcgactt    1380
gcatgtgtta agcctgccgc cagcgttcgt t                                    1411
```

METHYLOPILA SP. AND USE THEREOF IN SELECTIVE RESOLUTION PREPARATION OF (S)-α-ETHYL-2-OXO-1-PYRROLIDINEACETATE

CROSS-REFERENCE TO RELATED APPLICATIONS

This application is a National Phase Application of International Application No. PCT/CN2017/102275, filed Sep. 19, 2017, which claims the priority of Chinese Patent Application No. 201611106084.2, filed Dec. 5, 2016. The present application claims priority from both applications and each of these applications is herein incorporated in their entirety by reference.

TECHNICAL FIELD

The present invention relates to the field of biocatalysis technology, and in particular to *Methylopila* sp. and use thereof in the selective resolution preparation of (S)-α-ethyl-2-oxo-1-pyrrolidineacetate.

BACKGROUND ART

Levetiracetam has a chemical name of (S)-α-ethyl-2-oxo-1-acetamide pyrrolidine, which is a novel anti-epileptic drug belonging to acetylpyrrolidine compounds. The drug is not only high in therapeutic index, but also has unique pharmacokinetic characteristics of fast and safe oral absorption, and a bioavailability up to 100%, and thus is a broad-spectrum anti-epileptic drug with high efficacy and little side-effects and has a very high development value. It has been reported in the literature that dextroisomer (R)-α-ethyl-2-oxo-1-acetamide pyrrolidine has only a slight or insignificant pharmacodynamic effect on the inhibition of epilepsy, whereas levetiracetam is a safe and efficient anti-epileptic drug.

The key to the synthesis of levetiracetam is to control the optical purity of the laevoisomer during the reaction. (S)-α-ethyl-2-oxo-1-pyrrolidineacetic acid ethyl ester is subjected to ester hydrolysis to obtain (S)-α-ethyl-2-oxo-1-pyrrolidineacetic acid, and the acid in this configuration is a key chiral intermediate for the synthesis of levetiracetam and has a structural formula as follows:

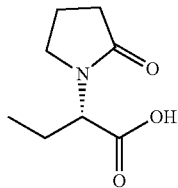

A single enantiomer can be prepared by chemical, enzymatic or chemo-enzymatic methods, etc. Early literatures introduce a preparation process for levetiracetam: reacting a racemic intermediate (±)-α-ethyl-2-oxo-1-pyrrolidineacetic acid of levetiracetam and an optically pure resolution reagent (R)-(+)-α-phenylethylamine or chiral phosphine to form a salt, and then cooling and crystallizing the same to separate the corresponding two enantiomers therefrom. The traditional enantiomeric separation process has the problems of high energy consumption, cumbersome operation, low yield, low product purity and serious environmental pollution, etc., which is not conducive to the energy conservation and emission reduction of pharmaceutical enterprises.

Compared with the chemical method, the biocatalysis has the advantages that the catalytic reaction usually shows a high stereoselectivity and regioselectivity, and the advantages of mild catalytic conditions, low energy consumption and high efficiency. Chinese patent "Tsukamurella tyrosinosolvens and catalytic preparation of (S)-α-ethyl-2-oxo-1-pyrrolidineacetic acid thereby" (Publication No. CN 101748087A) discloses Tsukamurella tyrosinosolvens which can be used in the chiral biocatalytic preparation of (S)-α-ethyl-2-oxo-1-pyrrolidineacetic acid, the yield of this method reaches 48.1%, but the reaction time is excessively long (12-60 h), the reaction substrate concentration is excessively low (a racemic substrate concentration of 5.2-31.2 g/L), the enzyme dosage is excessively large (5.2-31.2 g/L of wet bacterial cells), and it is difficult to achieve industrial production. Chinese Patent Application "Method and strain for microbial catalytic preparation of (S)-α-ethyl-2-oxo-1-pyrrolidineacetic acid ester" (Publication No. CN102994429A) discloses a Bacillus cereus, and a method in which with racemic α-ethyl-2-oxo-1-pyrrolidineacetic acid ester as a substrate, an ester hydrolase produced by this bacterium catalyses the stereoselective hydrolysis of (R)-α-ethyl-2-oxo-1-pyrrolidineacetic acid ester to obtain an S-configuration product, the maximum substrate dosage in this technique is only 100 g/L, the reaction time is up to 60 h, the highest yield is 48.9%, and it is difficult to apply this technique to industrialized production.

SUMMARY OF THE INVENTION

Object of the invention: the object of the present invention is to provide a new *Methylopila* sp.; and still another object of the present invention is to provide the use of the aforementioned *Methylopila* sp. in the stereoselective resolution preparation of (S)-α-ethyl-2-oxo-1-pyrrolidineacetate for application to industrial large-scale production.

Technical solution: for the *Methylopila* sp. cxzy-L013, this strain is deposited in China Center for Type Culture Collection (CCTCC), address: Wuhan University, Wuhan 430072, P. R. China, on Sep. 18, 2016, under the conservation number CCTCC M2016494.

The *Methylopila* sp. cxzy-L013 is obtained from the soil in the factory area of Huahai Pharmaceutical Co., Ltd., Duqiao Town, Linhai City, Zhejiang Province, by preliminary screening of colony characteristics on plates, using primary fermentation and shake-flask culture one by one, detecting the enzymatic activity, and comparing the enzymatic activity of the stereoselective ester hydrolases.

The morphology of colonies: after culturing on an LB agar plate at 30° C. for 48-72 h, the colonies are regularly rounded, and have neat edges, diameters of 0.5-1 mm and raised surfaces, and are moist, shiny and milky white; the cells are in short round rod shapes, and are singly and dispersively arranged with a size of (0.3-0.4) μm×(1.0-1.2) μm; Gram-negative bacteria; especially, they grow slowly on a medium when using glucose, glycerol and ethanol as carbon sources, and grow faster when using methanol, methylamine hydrochloride and ammonium formate as carbon sources. The 16SrDNA sequence listing of *Methylopila* sp. cxzy-L013 is as shown in SEQ ID NO. 1.

The present invention provides the use of the aforementioned *Methylopila* sp. cxzy-L013 in the stereoselective resolution preparation of (S)-α-ethyl-2-oxo-1-pyrrolidineacetate. It also provides a method for the stereoselective resolution preparation of (S)-α-ethyl-2-oxo-1-pyrrolidineacetate by the *Methylopila* sp. cxzy-L013, which specifically comprises the following steps:

(1) treating a bacterial solution of *Methylopila* sp. cxzy-L013 by a cell immobilization method to obtain an immobilized bacterial agent containing an immobilized resolution enzyme;

(2) with (R,S)-α-ethyl-2-oxo-1-pyrrolidineacetic acid ethyl ester as a substrate, adding a certain amount of water and the immobilized bacterial agent for a resolution reaction to obtain (S)-α-ethyl-2-oxo-1-pyrrolidineacetic acid ethyl ester; and (3) then using immobilized ester hydrolase hydrolysis or alkaline hydrolysis to obtain (S)-α-ethyl-2-oxo-1-pyrrolidineacetate.

The bacterial solution of *Methylopila* sp. cxzy-L013 is an enzyme-containing bacterial suspension containing not less than 50 wt % of wet cells, which is obtained by subjecting the *Methylopila* sp. cxzy-L013 to slant culture, seed liquid culture, inoculation fermentation and concentration steps. The specific obtaining steps are as follows:

Slant Culture

The *Methylopila* sp. cxzy-L013 strain in a glycerol tube is streaked on an LB slant test tube and is cultured at 30° C. for 2-3 days.

Seed Liquid Culture

The slant cells are inoculated into a seed culture medium, and cultured at 30° C. for 2-3 days, so as to obtain a seed liquid; and the concentrations and compositions of the seed medium are: $MgSO_4.7H_2O$ 1.0 g/L, $K_2HPO_4$ 1.8 g/L, $(NH_4)_2SO_4$ 1.0 g/L, yeast leaching powder 5.0 g/L, a methanol solution with a volume fraction of 75% 5.0 mL/L (added before inoculation), and ammonia water is used to adjust the pH to 7.0.

Inoculation Fermentation

The seed liquid is inoculated into a fermentation tank for fermentation: inoculation volume: 1-10 v/v %, fermentation temperature: 30° C., pH controlled by ammonia water: 6.5-7.0, aeration rate: 0.5-1 vvm, mechanical stirring speed: 100-1000 r/min, concentration of 75% methanol intermittently supplemented during fermentation: 5.0 mL/L, and fermentation time: 3-4 days; when the pH does not fall but rise, the cells are released from the tank and collected; and at this time OD600≥40, the wet weight of the cells can be up to 70-90 g/L.

The concentrations and compositions of the fermentation medium are: NaCl 0.5 g/L, $MgSO_4.7H_2O$ 3.6 g/L, $K_2HPO_4$ 1.0 g/L, $(NH_4)_2SO_4$ 1.0 g/L, yeast extract powder 6.0 g, and a methanol solution with a volume fraction of 75% 5.0 mL/L (added before inoculation).

In the present invention, the carbon source of the medium in the inoculation culture may be optionally selected from any one of methanol, methylamine hydrochloride and ammonium formate, preferably methanol. If the carbon source is changed to glucose, glycerol or ethanol, the cell growth is very slow.

In order to obtain an enzyme-containing bacterial suspension of not less than 50 wt %, enzyme-containing wet cells are obtained after centrifugal separation of the fermentation broth with a high-speed centrifuge; according to an equal mass ratio, the wet cells are diluted with water, stirred uniformly, and refrigerated for use; or the fermented broth is directly filtered and concentrated through a microfiltration membrane to obtain a bacterial suspension containing wet cells in a mass fraction of about 50 wt %, which is refrigerated for use.

The cell immobilization method comprises dissolving the bacterial solution of *Methylopila* sp. cxzy-L013 in a buffer solution, adding at least one adsorbent and/or cross-linking agent, and stirring and suction-filtrating the same to obtain the immobilized bacterial agent containing an immobilized resolution enzyme; the adsorbent is selected from any one of diatomaceous earth and activated carbon; and the cross-linking agent is selected from any one of glutaraldehyde, toluene diisocyanate and bis-diazotized benzidine. The immobilized resolution enzyme achieved by using the immobilization method has an enzyme activity recovery of not less than 90% and an adsorption rate of not lower than 95%, and the number of reuse times of the immobilized bacterial agent is not lower than 35.

The enzyme activity recovery after cell or enzyme immobilization has a calculation formula of:

$$A=W_0/(W_1-W_2)*100\%$$

wherein A is the enzyme activity recovery of the immobilized resolution enzyme, $W_1$ is the total activity of free enzymes added, $W_2$ is the total enzyme activity of the supernatant after immobilization, and $W_0$ is the total enzyme activity of the immobilized resolution enzyme.

The adsorption rate after cell or enzyme immobilization has a calculation formula of:

$$B=(W_1-W_2)/W_1*100\%$$

wherein B is the adsorption rate of the immobilized resolution enzyme, $W_1$ is the total activity of free enzymes added, and $W_2$ is the enzyme activity of the supernatant after immobilization.

In the cell immobilization technology, the embedding method, the crosslinking method, the adsorption method and the covalent immobilization method are common technical means. The embedding method generally uses sodium alginate and carrageenan, etc. to embed cells or enzymes, but the embedded immobilized particles have a small mechanical strength, and are easy to break up in the process of mixing. The adsorption method is simple in operation, easily achieves immobilization, and has mild conditions and cheap and readily available immobilization carriers that can be reused, but the adsorbed enzymes or cells are limited in number, have a weak binding capacity to the carrier, and thus are easy to fall off, resulting in decreased activity and contamination of reaction products. In the covalent binding method, the functional groups such as amino, carboxyl, phenolic, thiol, hydroxyl and imidazole groups, etc. in the enzyme can participate in covalent binding, wherein amino and carboxyl binding methods are the most common. The binding between the enzyme and carrier in the immobilized enzyme obtained by the method is firm and an enzyme shedding phenomenon is less prone to occur, but the advanced structure of enzyme protein is easily destroyed under more violent reaction conditions. The immobilized cells or enzymes prepared by the cross-linking method have good stability and can be used for a long time; glutaraldehyde is the most common cross-linking agent, which achieves the purpose of stabilizing cell or enzyme structures through a Schiff base reaction between small molecule substances with a bifunctional aldehyde group and the amino functional group on the cells or enzymes, so as to cross-link the cells or enzymes, but the immobilized cells by using a single cross-linking method has poor looseness, and it is difficult to achieve the effective separation of immobilized cells from the reaction solution in the catalytic reaction.

As a further optimization of the present invention, the cell immobilization method consists in first adding the adsorbent, and after stirring and mixing uniformly, then adding the crosslinking agent. First using the adsorption method to form embedded balls, and then using the cross-linking method in combination can significantly increase the mechanical strength and improve the stability.

As a further optimization of the present invention, polyethyleneimine is also added during the addition of the crosslinking agent. Polyethyleneimine has high adhesion and adsorption, and the amino group thereof can react with the hydroxyl group in cell or enzyme molecules to form a hydrogen bond, react with the carboxyl group to form an ionic bond, and also react with the carbonyl group to form a covalent bond; at the same time, polyethyleneimine can be combined with different substances due to the structure having a polar group (amido) and a hydrophobic group (vinyl).

As an optimal solution of the present invention, the cell immobilization steps comprise: dissolving 20 g of a bacterial suspension containing wet cells in a mass fraction of about 50 wt % in 100 mL of an ammonium formate buffer solution (pH 7.0), stirring and mixing the same uniformly, adding 0.6 g of diatomaceous earth or activated carbon, adding 3 mL of 5% polyethyleneimine for cross-linking for 1 h, then adding 1 mL of 25% glutaraldehyde for cross-linking for 1 h, and finally suction-filtering under vacuum to obtain the immobilized bacterial agent, washing the same with tap water twice, suction-filtrating and placing the same at 4° C. for refrigerated preservation.

Through the combined use of glutaraldehyde and polyethylenimine, the aldehyde group of glutaraldehyde and the amino group of polyethylenimine are polymerized to form a dense network structure to wrap the bacterial cells. The addition of diatomaceous earth contributes to the adsorption while increasing the particle size and looseness of the immobilized enzyme, allowing the immobilized particles to be more easily separated.

The immobilized bacterial agent containing the immobilized resolution enzyme obtained by using the above-mentioned cell immobilization method performs resolution on the racemate substrate, which can greatly increase the concentration of the substrate, thereby making industrial mass production possible. The (R,S)-α-ethyl-2-oxo-1-pyrrolidineacetic acid ethyl ester is 500-900 g/L in a toluene solution, preferably at a concentration of 700-800 g/L.

The conditions of the resolution reaction in step 2 are as follows: the reaction temperature is 25-37° C., a 15-25 v/v % aqueous sodium carbonate solution is dropwise added to control the pH of the reaction process at 6.5-8.5, and the reaction is carried out for 2-15 h.

Further, the mass concentration of (R,S)-α-ethyl-2-oxo-1-pyrrolidineacetic acid ethyl ester in the reaction system is 160-500 g/L. The immobilized bacterial agent has a dosage concentration of 5-25 g/L on a wet weight basis in the reaction system.

After the completion of the resolution reaction, the reaction conversion result is detected by HPLC, wherein the enantiomeric excess value $e.e._s$ (%) is not less than 99.5 and the conversion rate is not lower than 49%.

After the resolution reaction, a separation and purification method for the reaction mixture is as follows: the reaction solution is directly centrifuged by a high-speed centrifuge or filtered through a plate filter. After the liquid is partially layered, the organic phases are retained, and 1:0.3-1.5 of toluene is added to the aqueous layer for extraction 3-5 times. The organic phases are combined and the toluene is distilled off at 35-60° C., so as to obtain a concentrate (S)-α-ethyl-2-oxo-1-pyrrolidineacetic acid ethyl ester.

As a further optimization of the present invention, after step (2), the (R)-α-ethyl-2-oxo-1-pyrrolidineacetic acid in the aqueous phase is recovered, and is subjected to racemization and esterification to obtain the starting substrate material.

For the obtained (S)-α-ethyl-2-oxo-1-pyrrolidineacetic acid ethyl ester, the salt of (S)-α-ethyl-2-oxo-1-pyrrolidineacetic acid can be obtained again by an enzyme hydrolysis method using the immobilized ester hydrolase: adding 1 part of industrial water and 1-2 parts of a concentrate of (S)-α-ethyl-2-oxo-1-pyrrolidineacetic acid ethyl ester to a reactor, adding 1/20-1/5 parts of the immobilized ester hydrolase, stirring, controlling the temperature and pH until the ester hydrolysis reaction is finished, filtering off the immobilizd ester hydrolase to obtain a salt solution of (S)-α-ethyl-2-oxo-1-pyrrolidineacetic acid, followed by concentration and crystallization to obtain a solid crude product of (S)-α-ethyl-2-oxo-1-pyrrolidineacetate.

Again, it should be noted that the immobilized ester hydrolase differs from the immobilized enzyme mentioned above in concept. The aforementioned immobilized resolution enzyme is produced by the *Methylopila* sp. cxzy-L013 strain of the present invention and has the racemic substrate (R,S)-α-ethyl-2-oxo-1-pyrrolidineacetic acid ethyl ester subjected to specific resolution, in which (R)-α-ethyl-2-oxo-1-pyrrolidineacetic acid ethyl ester is hydrolyzed to (R)-α-ethyl-2-oxo-1-pyrrolidineacetic acid which is dissolved in water to obtain a water-insoluble corresponding single isomer (S)-α-ethyl-2-oxo-1-pyrrolidineacetic acid ethyl ester; however, the immobilized ester hydrolase is universal and used in the present invention to hydrolyze the ester bond of (S)-α-ethyl-2-oxo-1-pyrrolidineacetic acid ethyl ester, with reacting at the optimum temperature and pH of the enzyme, and the resultant salt solution is then concentrated and crystallized. The enzyme immobilization method includes, but is not limited to, any one of the existing embedding method, cross-linking method, covalent immobilization method and adsorption method, which can be selectively used according to the knowledge known by those skilled in the art and the teachings of the prior art. The purpose of immobilizing the immobilized ester hydrolase is to allow the obtained hydrolyzate (S)-α-ethyl-2-oxo-1-pyrrolidineacetate to contain less impurities, and more conducive to the separation of the crude product, so as to improve the single-pass yield and purity of the crude product.

For the obtained (S)-α-ethyl-2-oxo-1-pyrrolidineacetic acid ethyl ester, it is also possible to obtain the salt of (S)-α-ethyl-2-oxo-1-pyrrolidineacetic acid by an alkaline hydrolysis method: adding 2-3 parts of deionized water and 2-3 parts of the concentrate of (S)-α-ethyl-2-oxo-1-pyrrolidineacetic acid ethyl ester to a reactor, stirring, and then adding 1-2 parts of 200-400 g/L of an ionic membrane alkaline solution so that the pH of the reaction is not less than 13, hydrolyzing at 10-20° C. for 1-5 h until the hydrolysis reaction of the substrate is finished, so as to obtain a salt solution of (S)-α-ethyl-2-oxo-1-pyrrolidineacetic acid, followed by concentration and crystallization to obtain a solid crude product of (S)-α-ethyl-2-oxo-1-pyrrolidineacetate.

The present invention also provides a cell immobilized bacterial agent, which can be used to isolate (S)-α-ethyl-2-oxo-1-pyrrolidineacetic acid ethyl ester from its racemate solution. The immobilized enzyme of the cell immobilized bacterial agent has an activity recovery of not less than 90% and an adsorption rate of not lower than 95%, and the number of reuse times of the immobilized bacterial agent is not lower than 35. The bacterial agent is obtained by the following method:

dissolving the bacterial liquid of *Methylopila* sp. cxzy-L013 according to claim 1 into a buffer solution, adding at least one adsorbent and/or cross-linking agent, and stirring and suction-filtrating the same to obtain the immobilized bacterial agent, wherein the adsorbent is selected from any one of diatomaceous earth and activated carbon; and the cross-linking agent is selected from any one of glutaraldehyde, toluene diisocyanate and bis-diazotized benzidine.

Preferably, the combined use of the adsorption method and the cross-linking method for cell immobilization can effectively increase the enzyme activity recovery rate and the adsorption rate of the immobilized enzyme.

Furthermore, after the adsorbent is added, polyethyleneimine is first added, and then the cross-linking agent is added; the adsorbent is selected from diatomaceous earth, and the cross-linking agent is selected from glutaraldehyde.

Beneficial effects: the enzyme produced by the *Methylopila* sp. xczy-L013 strain obtained by isolation and screening in the present invention has an extremely high stereoselectivity for the hydrolysis reaction of the racemic substrate (R,S)-α-ethyl-2-oxo-1-pyrrolidineacetic acid ethyl ester, which is first discovered in the fermentation engineering application of the microorganisms of *Methylopila* sp. The bacterial cells producing enzymes, which are fermented from the *Methylopila* sp. cxzy-L013 strain, are subjected to an improved immobilization process, and the immobilized bacterial agent is used to perform a stereoselective ester hydrolysis reaction on the racemic substrate (R,S)-α-ethyl-2-oxo-1-pyrrolidineacetic acid ethyl ester under certain conditions; a high conversion yield up to 50.0% or more is achieved, the stereoselectivity is good, and the enantiomeric excess value e.e.$_s$ (%) of (S)-α-ethyl-2-oxo-1-pyrrolidineacetic acid ethyl ester is not less than 99.5; the catalytic efficiency is high; the concentration of the racemic substrate in the resolution reaction is up to 500 g/L, the reaction time does not exceed 15 h, the number of reuse times of the immobilized cells is not lower than 35, and thus the present invention is convenient for industrial production, is simple in downstream separation and produces little environmental pollution.

DETAILED DESCRIPTION OF EMBODIMENTS

Figure 1:
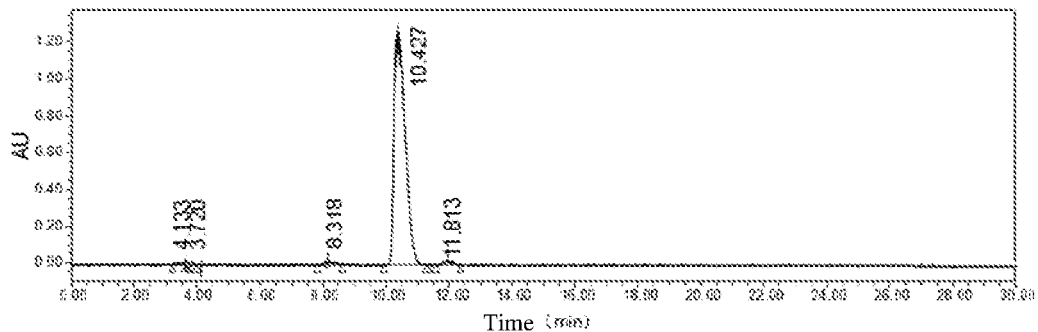
FIG. 1 is a peak appearance chromatogram of (S)-α-ethyl-2-oxo-1-pyrrolidineacetic acid.
Figure 2:
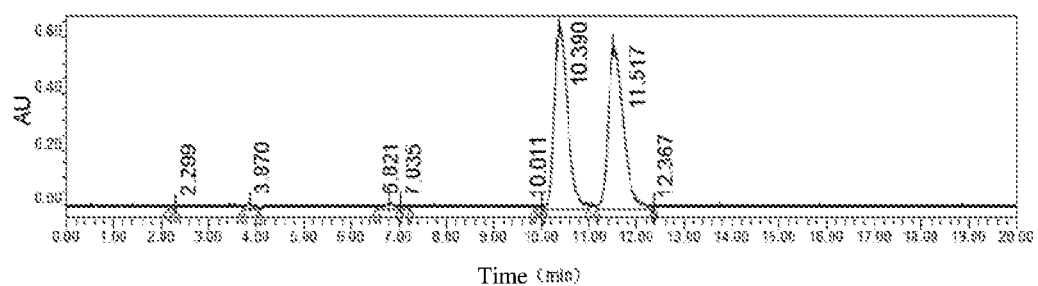
FIG. 2 is a peak appearance chromatogram of racemic (R,S)-α-ethyl-2-oxo-1-pyrrolidineacetic acid.
Figure 3:
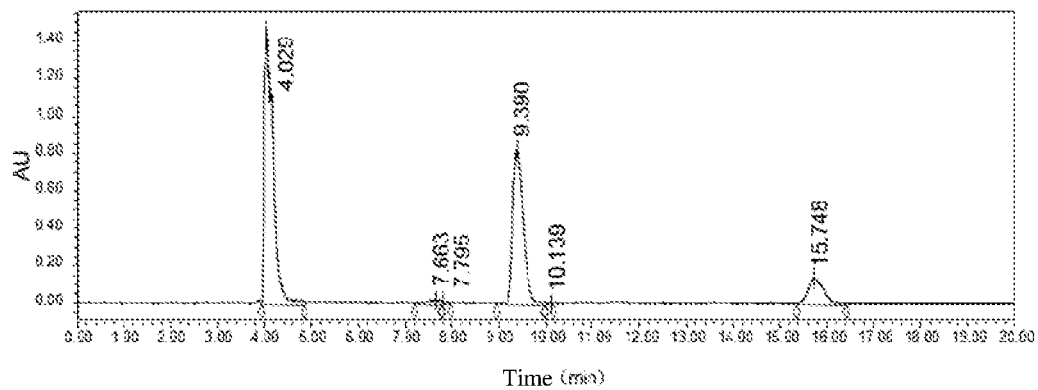
FIG. 3 is an HPLC chromatogram of an organic phase after the catalytic resolution of racemic (R,S)-α-ethyl-2-oxo-1-pyrrolidineacetic acid ethyl ester for 3 h.
Figure 4:
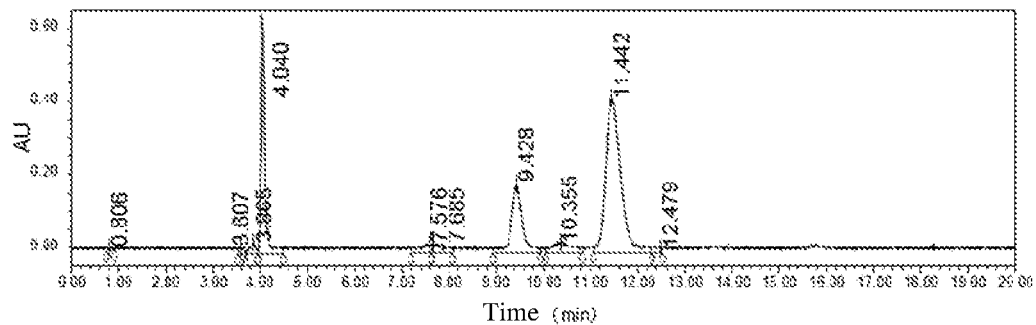
FIG. 4 is an HPLC chromatogram of an aqueous phase after the catalytic resolution of racemic (R,S)-α-ethyl-2-oxo-1-pyrrolidineacetic acid ethyl ester for 3 h.

The present invention will be further described with reference to particular embodiments. It should be noted that unless otherwise specified, the percentage concentrations described below are mass percentage concentrations.

Example 1

*Methylopila* sp. cxzy-L013, which strain is deposited in China Center for Type Culture Collection (CCTCC), address: Wuhan University, Wuhan 430072, P. R. China, on Sep. 18, 2016, under the conservation number CCTCC M2016494.

The *Methylopila* sp. cxzy-L013 is obtained from the soil in the factory area of Huahai Pharmaceutical Co., Ltd., Duqiao Town, Linhai City, Zhejiang Province, by preliminary screening of colony characteristics on plates, using primary fermentation and shake-flask culture one by one, detecting the enzymatic activity, and comparing the enzymatic activity of the stereoselective ester hydrolases.

The characteristics of the colonies are as follows: colonies are regularly rounded, and have neat edges, diameters of 0.5-1 mm and raised surfaces, and are moist, shiny and milky white; the cells are in short round rod shapes, and are singly and dispersively arranged with a size of (0.3-0.4) μm×(1.0-1.2) μm; Gram-negative bacteria; especially, they grow slowly on a medium when using glucose, glycerol and ethanol as carbon sources, and grow faster when using methanol, methylamine hydrochloride and ammonium formate as carbon sources.

Example 2

The *Methylopila* sp. cxzy-L013 obtained in example 1 should be further activated through culturing for fermentation to obtain a bacterial liquid of *Methylopila* sp. cxzy-L013. The specific obtaining steps are as follows:

Slant Culture

The *Methylopila* sp. cxzy-L013 strain in a glycerol tube is streaked on an LB slant test tube and is cultured at 30° C. for 2-3 days.

Seed Liquid Culture

The slant cells are inoculated into a seed culture medium, and cultured at 30° C. for 2-3 days, so as to obtain a seed liquid; and the concentrations and compositions of the seed medium are: $MgSO_4 \cdot 7H_2O$ 1.0 g/L, $K_2HPO_4$ 1.8 g/L, $(NH_4)_2SO_4$ 1.0 g/L, yeast leaching powder 5.0 g/L, a methanol solution with a volume fraction of 75% 5.0 mL/L (added before inoculation), and ammonia water is used to adjust the pH to 7.0.

Inoculation Fermentation

The seed liquid is inoculated into a 7 L fermentation tank for fermentation: inoculation volume: 100 mL, initial volume of the fermentation broth: 5 L, fermentation temperature: 30° C., pH controlled by ammonia water: 6.5-7.0, aeration rate: 0.5-1 vvm, gradually increasing the mechanical stirring speed from 100 r/min to 900 r/min, so that DO≥30%, concentration of 75% methanol intermittently supplemented during fermentation: 5.0 mL/L, and fermentation time: 3-4 days; when the pH does not fall but rise, the cells are released from the tank and collected; and at this time OD600≥40, the wet weight of the cells can be up to 70-90 g/L.

The concentrations and compositions of the fermentation medium are: NaCl 0.5 g/L, $MgSO_4 \cdot 7H_2O$ 3.6 g/L, $K_2HPO_4$ 1.0 g/L, $(NH_4)_2SO_4$ 1.0 g/L, yeast extract powder 6.0 g, a methanol solution with a volume fraction of 75% 5.0 mL/L (added before inoculation).

As shown in Table 1, when the methanol used in the fermentation process is changed to use glucose, glycerol and ethanol as a carbon source, the cell growth is very slow, and it can be seen that methanol as the carbon source is significantly superior to the other three carbon sources. The medium formulation used is the same as the medium formulation of the seed liquid medium except for the carbon source, and the culture method is also the same as that for the seed liquid culture.

TABLE 1

Effects of different carbon sources in the fermentation of the bacterial solution

| Carbon source type | Carbon source concentration | Fermentation method | Cell concentration $OD_{600}$ |
|---|---|---|---|
| methanol with a volume fraction of 75% | 5.0 mL/L | shake-flask fermentation | 5 ± 0.5 |
| glucose | 5 g/L | shake-flask fermentation | 2 ± 0.5 |
| glycerol | 5 g/L | shake-flask fermentation | 1 ± 0.5 |
| ethanol with a volume fraction of 75% | 5.0 mL/L | shake-flask fermentation | 2 ± 0.5 |

As shown in Table 2, if the yeast extract powder in the fermentation medium is changed to use corn steep liquor powder, tryptone, beef extract or the like as a carbon source, the growth rate of the cell is common, and the yeast extract powder is superior to the other three carbon sources. The medium formulation used is the same as the medium formulation of the seed liquid medium except for the nitrogen source, and the culture method is also the same as that for the seed liquid culture.

TABLE 2

Effects of different carbon sources as the carbon source of the fermentation medium for the bacterial solution

| Carbon source type | Carbon source concentration | Fermentation method | Cell concentration $OD_{600}$ |
|---|---|---|---|
| yeast extract powder | 6 g/L | shake-flask fermentation | 5 ± 0.5 |
| corn steep liquor powder | 6 g/L | shake-flask fermentation | 3.5 ± 0.5 |
| beef extract | 6 g/L | shake-flask fermentation | 2 ± 0.5 |
| tryptone | 6 g/L | shake-flask fermentation | 2.5 ± 0.5 |

In order to obtain an enzyme-containing bacterial suspension of not less than 50 wt %, enzyme-containing wet cells are obtained after centrifugal separation of the fermentation broth with a high-speed centrifuge; according to an equal mass ratio, the wet cells are diluted with water, stirred uniformly, and refrigerated for use; or the fermented broth is directly filtered and concentrated through a microfiltration membrane to obtain a bacterial suspension containing wet cells in a mass fraction of about 50 wt %, which is refrigerated for use.

Example 3

(S)-α-ethyl-2-oxo-1-pyrrolidineacetate is prepared by stereoselective resolution using *Methylopila* sp. cxzy-L013 of example 1, comprising the following steps:
(1) treating a bacterial solution of *Methylopila* sp. cxzy-L013 by a cell immobilization method to obtain an immobilized bacterial agent containing an immobilized resolution enzyme, wherein the method for obtaining the bacterial solution of *Methylopila* sp. cxzy-L013 has been set forth in example 2;
(2) with (R,S)-α-ethyl-2-oxo-1-pyrrolidineacetic acid ethyl ester as a substrate, adding a certain amount of water and the immobilized bacterial agent for a resolution reaction to obtain (S)-α-ethyl-2-oxo-1-pyrrolidineacetic acid ethyl ester; and
(3) using immobilized ester hydrolase hydrolysis or alkaline hydrolysis to obtain (S)-α-ethyl-2-oxo-1-pyrrolidineacetate.
(4) after step (2), recovering the (R)-α-ethyl-2-oxo-1-pyrrolidineacetic acid in the aqueous phase, and performing racemization and esterification to obtain the starting substrate material.

The cell immobilization method in step (1) consists of first adding the adsorbent, and after stirring and mixing uniformly, then adding the crosslinking agent. The mechanical strength can be significantly increased by first using the adsorption method to form embedded balls, and then using the cross-linking method in combination. The immobilized resolution enzyme achieved by the cell immobilization method has an enzyme activity recovery of not less than 90% and an adsorption rate of not lower than 95%, and the number of reuse times of the immobilized bacterial agent is not lower than 35.

In step (2), the (R,S)-α-ethyl-2-oxo-1-pyrrolidineacetic acid ethyl ester is 500-900 g/L in a toluene solution, preferably at a concentration of 700-800 g/L. The mass concentration of (R,S)-α-ethyl-2-oxo-1-pyrrolidineacetic acid ethyl ester in the reaction system is 160-500 g/L. The immobilized bacterial agent has a dosage concentration of 5-25 g/L on a wet weight basis in the reaction system.

The conditions of the resolution reaction are as follows: the reaction temperature is 25-37° C., an aqueous solution of sodium carbonate with a volume fraction of 15-25% (V/V) is dropwise added to control the pH of the reaction process at 6.5-8.5, the reaction is carried out for 2-15 h, the reaction conversion result is detected by HPLC, the enantiomeric excess value $e.e._s$ (%) is not less than 99.5, and the conversion rate is up to 50%.

After the resolution reaction, a separation and purification method for the reaction mixture is as follows: the reaction solution is directly centrifuged by a high-speed centrifuge or filtered through a plate filter. After the liquid is partially layered, the organic phases are retained, and 1:0.3-1.5 of toluene is added to the aqueous layer for extraction 3-5 times. The organic phases are combined and the toluene is distilled off at 35-60° C., so as to obtain a concentrate of (S)-α-ethyl-2-oxo-1-pyrrolidineacetic acid ethyl ester.

Any of the immobilized ester hydrolases capable of hydrolyzing the (S)-α-ethyl-2-oxo-1-pyrrolidineacetic acid ethyl ester ester bond can be used in step (3). 1 part of industrial water and 1-2 parts of a concentrate of (S)-α-ethyl-2-oxo-1-pyrrolidineacetic acid ethyl ester are added to a reactor, 1/20-1/5 parts of the immobilized ester hydrolase are added and stirred, the temperature and pH are controlled until the ester hydrolysis reaction is finished, the ester hydrolase is filtered off to obtain a salt solution of (S)-α-ethyl-2-oxo-1-pyrrolidineacetic acid, which is then subjected to concentration and crystallization to obtain a solid crude product of (S)-α-ethyl-2-oxo-1-pyrrolidineacetate.

In step (3), for the obtained (S)-α-ethyl-2-oxo-1-pyrrolidineacetic acid ethyl ester, it is also possible to obtain the salt of (S)-α-ethyl-2-oxo-1-pyrrolidineacetic acid by an alkaline hydrolysis method: adding 2-3 parts of deionized water and 2-3 parts of the concentrate of (S)-α-ethyl-2-oxo-1-pyrrolidineacetic acid ethyl ester to a reactor, stirring, and then adding 1-2 parts of 300 g/L of an ionic membrane alkaline solution so that the pH reaches 14, hydrolyzing at 10-20° C. for 1-5 h until the hydrolysis reaction of the substrate is finished, so as to obtain a salt solution of (S)-α-ethyl-2-oxo-1-pyrrolidineacetic acid, followed by concentration and crystallization to obtain a solid crude product of (S)-α-ethyl-2-oxo-1-pyrrolidineacetate.

Example 4

Based on example 3, this example further optimizes the cell immobilization method in step (1): with 20 g of a bacterial suspension containing wet cells dissolved in a mass fraction of 50 wt % in 100 mL of an ammonium formate buffer solution (pH 7.0) for reaction as a preferred example, stirring and mixing the same uniformly, adding 0.4-0.8 g of diatomaceous earth or activated carbon, adding 3-4.5 mL of 5% polyethyleneimine for cross-linking for 1 h, then adding 1-1.5 mL of 25% glutaraldehyde for cross-linking for 1 h, and finally filtering under vacuum to obtain an immobilized bacterial agent containing the immobilized resolution enzyme, washing same with tap water 2 times, suction-filtrating and placing same at 4° C. for refrigerated preservation. The immobilized resolution enzyme has an enzyme activity recovery≥90% and an adsorption rate≥95%.

Example 5

Based on the method of example 3, this example selects Protin AP Conc. lipase from Amano Enzyme Inc., Janpan as an immobilized ester hydrolase to obtain (S)-α-ethyl-2-oxo-1-pyrrolidineacetate.

2 g of a Protin AP Conc. lipase powder is dissolved in 100 mL of purified water, 2 g of sodium alginate is added and slowly stirred until completely dissolved, and the mixed solution is uniformly pumped with a needle or sprayer into a 100 mM calcium chloride solution, and is slowly stirred until the bead-like gel is hardened, and then is repeatedly washed with distilled water 2-3 times to obtain an ester hydrolase immobilized by calcium alginate, which is preserved at 4° C. for use.

Example 6

A cell immobilized bacterial agent can be used to isolate (S)-α-ethyl-2-oxo-1-pyrrolidineacetic acid ethyl ester from its racemate solution. The immobilized resolution enzyme has an activity recovery of not less than 90% and an adsorption rate of not lower than 95%, and the number of reuse times of the immobilized bacterial agent is not lower than 35. The bacterial agent is obtained by the following method:

The bacterial suspension of *Methylopila* sp. cxzy-L013 as described in example 2 is dissolved in a buffer solution, diatomaceous earth is at least added as an adsorbent, then polyethyleneimine is added, then glutaraldehyde is added as a cross-linking agent, and an immobilized cell solution is obtained after stirring. The immobilized bacterial agent is obtained by vacuum filtration. The specific method is described with reference to example 4.

Example 7

Based on example 3, this example further describes the step of resolution of (S)-α-ethyl-2-oxo-1-pyrrolidineacetic acid ethyl ester in step (2):

taking 300 mL of a catalytic reaction system as an example: 100 mL of a toluene solution with (R,S)-α-ethyl-2-oxo-1-pyrrolidineacetic acid ethyl ester at a concentration of about 500 g/L is used to prepare a cell immobilized bacterial agent according to the method of example 4 and example 6.

Specifically: 200 mL of water is added to a 500 mL conversion bottle, 100 mL of a toluene solution containing about 50 g of (R,S)-α-ethyl-2-oxo-1-pyrrolidineacetic acid ethyl ester is added to allow the initial concentration of (R,S)-α-ethyl-2-oxo-1-pyrrolidineacetic acid ethyl ester in the reaction system to be about 166 g/L, stirring is initiated, a $Na_2CO_3$ solution (20%, V/V) is used to adjust the pH to 7.0, 2 g of the cell immobilized bacterial agent prepared in example 6 is added, the immobilization bacterial agent has a dosage concentration of 6.6 g/L, at 37° C., the $Na_2CO_3$ solution (20%, V/V) is used to maintain the pH at 7.0-7.5, and the resolution reaction is carried out for 2-3 h. The reaction conversion result is detected by HPLC, the enantiomeric excess value $e.e._s$ (%) is not less than 99.8 and the conversion rate is 50.0%.

Examples 8-13

The resolution method in examples 8-13 is basically the same as that in example 7, except that the dosage of the cell immobilized bacterial agent, the concentration of the substrate used in the toluene solution, and the concentration of the substrate in the reaction system are different. The differences in resolution effect of different examples can be seen from Table 3.

TABLE 3

Results for biocatalytic resolution of the substrate (R,S)-α-ethyl-2-oxo-1-pyrrolidineacetic acid ethyl ester

| Examples | Dosage concentration of the immobilized bacterial agent (g/L) | Concentration of the substrate in toluene (g/L) | Initial concentration of the substrate in the reaction system (g/L) | Resolution time (h) | Main product configuration | Enantiomeric excess value $e.e._s$ (%) | Conversion rate C (%) |
|---|---|---|---|---|---|---|---|
| Example 8 | 6.6 | 500 | 166 | 2-3 | S | 99.8 | 50.0 |
| Example 9 | 16.6 | 500 | 250 | 2-3 | S | 99.9 | 49.1 |
| Example 10 | 16.6 | 500 | 333 | 10-12 | S | 99.6 | 49.5 |
| Example 11 | 16.6 | 600 | 200 | 5-6 | S | 99.9 | 49.8 |

TABLE 3-continued

Results for biocatalytic resolution of the substrate
(R,S)-α-ethyl-2-oxo-1-pyrrolidineacetic acid ethyl ester

| Examples | Dosage concentration of the immobilized bacterial agent (g/L) | Concentration of the substrate in toluene (g/L) | Initial concentration of the substrate in the reaction system (g/L) | Resolution time (h) | Main product configuration | Enantiomeric excess value e.e.$_s$ (%) | Conversion rate C (%) |
|---|---|---|---|---|---|---|---|
| Example 12 | 25 | 800 | 400 | 8-9 | S | 99.8 | 49.8 |
| Example 13 | 25 | 800 | 533 | 12-14 | S | 99.9 | 50.0 |

Based on examples 8-13, it can be seen that: when the dosage of the toluene solution of the substrate is larger, the reaction time is longer, and the conversion rate is decreased; if the concentration of the substrate in the toluene solution is higher, and the dosage in the reaction system is larger, the reaction will be prolonged; and the conversion rate can still achieve the desired effect by a method of appropriately increasing the dosage of the immobilized bacterial agent.

Test Example 1

Resolution Reaction Liquid Monitoring

Instrument: high performance liquid chromatograph equipped with a UV detector

Chromatographic column: CHIRALPAK AS-H 250×4.6 mm 5 μm

Mobile phase: n-hexane:isopropanol:trifluoroacetic acid=80:20:0.2 (% V/V/V)

Flow rate: 0.8 mL/min, wavelength: 210 nm, column temperature: 30° C., running time: 30 min, injection volume: 20 μL Diluent: mobile phase, blank solution:diluent Test sample solution: 20 mg of the test sample is weighed into a 10 mL volumetric flask, and dissolved with a diluent to a fixed volume. The test sample comprises: racemic (R,S)-α-ethyl-2-oxo-1-pyrrolidineacetic acid ethyl ester and its monomers, and racemic (R,S)-α-ethyl-2-oxo-1-pyrrolidineacetic acid and its monomers.

Sample treatment: based on the method steps of example 4, the reaction solution is diluted by 100 folds, mixed uniformly and then filtered through a 0.45 μm microporous filter membrane, and is ready for injection.

The enantiomeric excess value e.e. and substrate conversion rate C of (S)-α-ethyl-2-oxo-1-pyrrolidineacetic acid ethyl ester are calculated according to the following equations:

$$e.e._s(\%) = \left|\frac{[C]_S - [C]_R}{[C]_S + [C]_R}\right| \times 100\%$$  Equation 1

$$C(\%) = \frac{C_P}{C_P + C_S} \times 100\%$$  Equation 2 in the equations, $[C]_S$ and $[C]_R$ are respectively the contents of S and R types of substrates in the sample measured by chromatography, e.e.$_s$ (%) is the enantiomeric excess value of (S)-α-ethyl-2-oxo-1-pyrrolidineacetic acid ethyl ester in the resolution reaction, $C_P$ is the molar concentration of the product, $C_S$ is the molar concentration of the remaining substrate, and C (%) is the conversion rate.

As can be seen from FIG. 1 to FIG. 6, (S)-α-ethyl-2-oxo-1-pyrrolidineacetic acid ethyl ester has a peak appearance time of 9.4 min, (R)-α-ethyl-2-oxo-1-pyrrolidineacetic acid ethyl ester has a peak appearance time of 15.9 min, (S)-α-ethyl-2-oxo-1-pyrrolidineacetic acid has a peak appearance time of 11.5 min, and (R)-α-ethyl-2-oxo-1-pyrrolidineacetic acid has a peak appearance time of 10.4 min.

Figure 5:
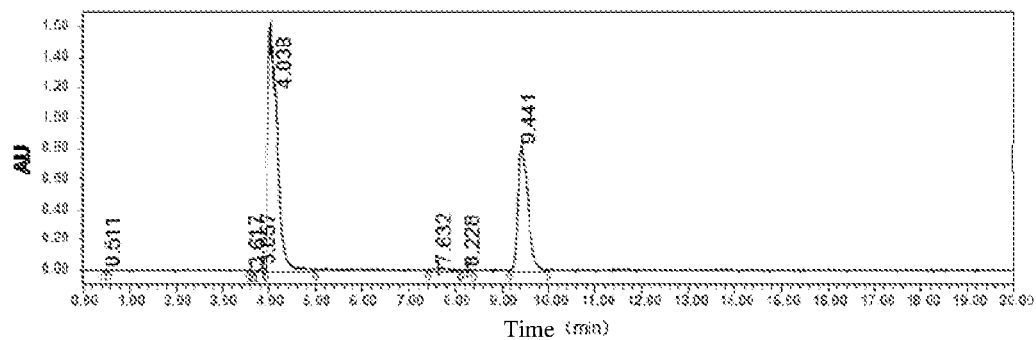
FIG. 5 is an HPLC chromatogram of an organic phase at the end of the catalytic resolution of racemic (R,S)-α-ethyl-2-oxo-1-pyrrolidineacetic acid ethyl ester.
Figure 6:
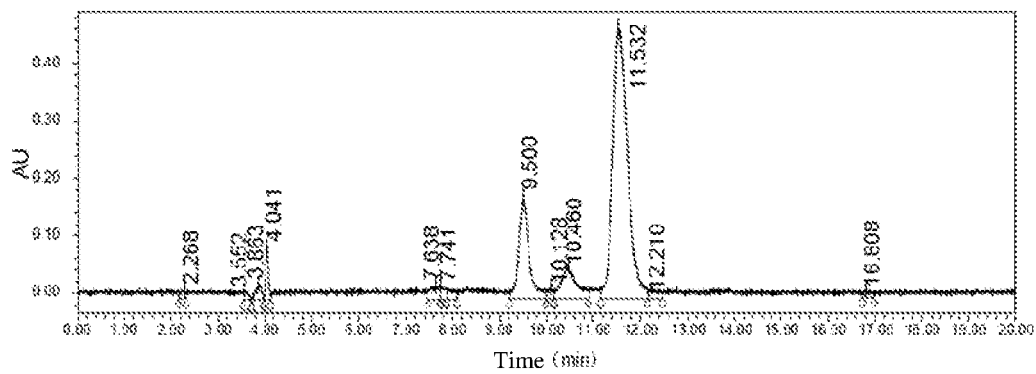
FIG. 6 is an HPLC chromatogram of an aqueous phase at the end of the catalytic resolution of racemic (R,S)-α-ethyl-2-oxo-1-pyrrolidineacetic acid ethyl ester.

FIG. 5 is an HPLC chromatogram of an organic phase at the end of the catalytic resolution of racemic (R,S)-α-ethyl-2-oxo-1-pyrrolidineacetic acid ethyl ester, and it can be seen that (R)-α-ethyl-2-oxo-1-pyrrolidineacetic acid ethyl ester has been completely hydrolyzed.

Test Example 2

Comparison of Immobilization Methods

In the present invention, the adsorbent and the cross-linking agent are simultaneously used in the immobilization method, polyethyleneimine in combination with glutaraldehyde improves the cross-linking effect, the immobilization effect of the cells is obviously improved, and then when they participate in an enzyme catalytic reaction with a high-concentration organic substrate, the purpose of industrial production is easily achieved.

Immobilization object: bacterial cells obtained after the fermentation of the *Methylopila* sp. cxzy-L013 strain of example 2, and an enzyme solution obtained by the ultrasonic disruption of the bacterial cells.

First of all, this test example compares the use of the adsorption method, the embedding method and the adsorption-cross-linking method, and describes the differences in immobilization effect of the enzyme in the cells caused by different treatment methods for the bacterial solution, the results being as shown in table 4:

TABLE 4

Influence of different immobilization methods and bacterial solution treatment methods on the immobilization effect

| Test group | Immobilization method | Immobilization object | Specific operation | Result |
|---|---|---|---|---|
| A | Epoxy resin adsorption | disrupted enzyme solution | 10 mL enzyme solution + 1 g resin, stirring at 25° C. for 12 h, and suction-filtrating | enzyme activity recovery ≥ 30% |
| B | Sodium alginate embedding | bacterial cells | 10 g bacterial cells + 2% sodium alginate, shaking uniformly, dorpwise adding the mixture to a 0.1 M/L calcium chloride solution, slowly stirring, and suction-filtrating | enzyme activity recovery ≥ 90%, but after repeating 5 times, enzyme activity decreases to 50% of the initial activity |
| C | Adsorption-cross-linking of polyethylenimine with glutaraldehyde | disrupted enzyme solution | 10 mL of bacterial solution + 0.6 g diatomaceous earth, successively adding 3 mL of 5% polyethyleneimine and 1 mL of 25% glutaraldehyde, stirring for 1 h, and suction-filtrating | suction-filtration cannot be performed after immobilization, indicating that the enzyme protein and the cross-linking agent are not fully cross-linked |
| D | Adsorption-cross-linking of polyethylenimine with glutaraldehyde | bacterial cells | 10 g bacterial cells + 0.6 g diatomaceous earth, successively adding 3 mL of 5% polyethyleneimine and 1 mL of 25% glutaraldehyde, stirring for 1 h, and suction-filtrating | Enzyme activity recovery ≥ 90%, adsorption rate after cell immobilization ≥ 95%; 19 batches are used repeatedly, and the activity of each batch of enzyme is stable |

Secondly, for test group D, an immobilization and optimization experiment is performed on the dosage of the adsorbent (diatomaceous earth or activated carbon) and the cross-linking agent, respectively, and the results are as shown in Table 5:

TABLE 5

Influence of different immobilization methods and bacterial solution treatment methods on the immobilization effect

| Test group | Adsorbent | Cross-linking agent 5% polyethyl-eneimine | Cross-linking agent 25% glutar-aldehyde | Result enzyme activity recovery | Result Adsorption rate after cell immobilization |
|---|---|---|---|---|---|
| D-1 | diatomaceous earth 0.4 g | 3 mL | 1 mL | 83% | 82% |
| D-2 | diatomaceous earth 0.6 g | 3 mL | 1 mL | 90% | 95% |
| D-3 | diatomaceous earth 0.8 g | 3 mL | 1 mL | 87% | 95% |
| D-4 | diatomaceous earth 0.6 g | 4.5 mL | 1.5 mL | 78% | 98% |
| D-5 | activated carbon 0.6 g | 3 mL | 1 mL | 81% | 95% |
| D-6 | activated carbon 0.6 g | 4.5 mL | 1.5 mL | 73% | 96% |

Test Example 3

Validation of the Number of Reuse Times after Cell Immobilization

Validation method: 100 mL of racemic (R,S)-α-ethyl-2-oxo-1-pyrrolidineacetic acid ethyl ester is catalyzed by 5 g of the immobilized bacterial agent obtained in example 4, and the content of the racemic substrate in toluene is 500 g/L, the reaction system is 300 mL, and the consumption of 30 mL of a $Na_2CO_3$ solution (20%, V/V) indicates the end of the reaction; and after the reaction is finished, the immobilized bacterial agent is suction-filtered and the suction-filtered immobilized bacterial agent is put into the same system and subjected to the next reaction under the same reaction conditions.

Figure 7:
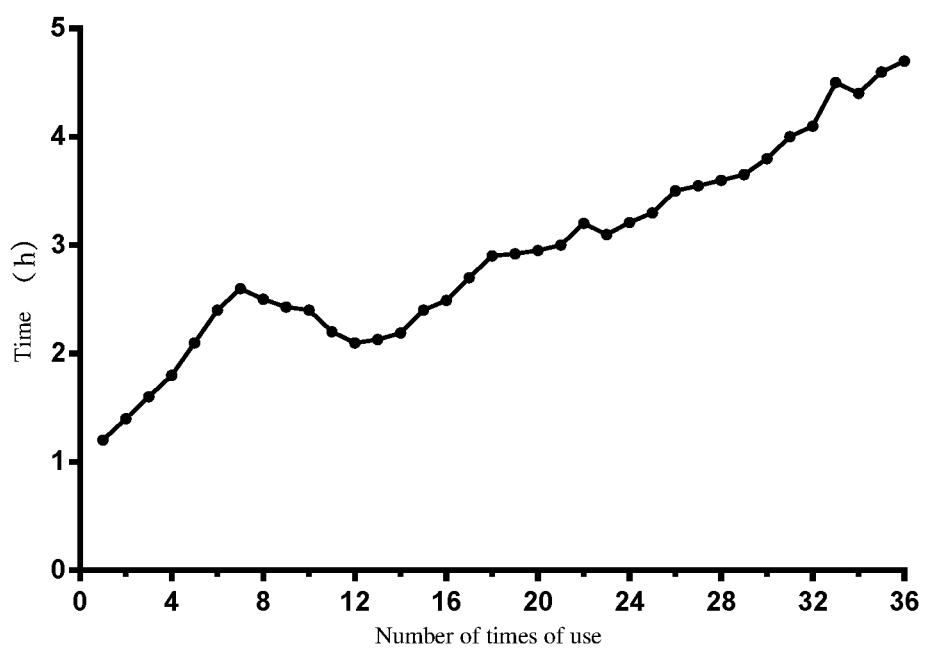
FIG. 7 shows a chart of changing trend of the reaction time as a function of the number of times of use of the enzyme in test example 3.

FIG. 7 shows a chart of changing trend of the time required to finish the reaction as the number of times of use increases. It can be seen from the figure that 1.2 h is required for finishing the 1st reaction, thereafter, the reaction time gradually increases, 2.6 h is required for the 7th reaction, however, the reaction time begins to decrease after the 8th reaction. Due to repeated filtration and weight loss of the enzyme, the overall reaction time after the 12th reaction tends to increase, but the reaction time is substantially maintained within 5 h after the cell immobilized bacterial agent is used 36 times, with an ideal effect as expected.

The above description is merely preferred embodiments of the present invention, and it should be noted that for a person skilled in the art, some improvements and modifications can also be made under the premise of not departing from the principle of the present invention, and these improvements and modifications are also considered to be within the scope of protection of the present invention.

The invention claimed is:

1. A method for a selective resolution preparation of (S)-α-ethyl-2-oxo-1-pyrrolidineacetate, comprising the following three steps:
    (1) immobilizing bacterial cells of *Methylopila* sp. in a cell immobilization method using a bacterial solution of *Methylopila* sp. to obtain an immobilized bacterial agent containing an immobilized resolution enzyme, wherein the *Methylopila* sp. is a *Methylopila* sp. cxzy-L013 strain deposited in China Center for Type Culture Collection on Sep. 18, 2016 under the conservation number CCTCC M2016494;
    (2) reacting (R,S)-α-ethyl-2-oxo-1-pyrrolidineacetic acid ethyl ester as a substrate with a predetermined amount of water and the immobilized bacterial agent to obtain (S)-α-ethyl-2-oxo-1-pyrrolidineacetic acid ethyl ester; and
    (3) hydrolysing (S)-α-ethyl-2-oxo-1-pyrrolidineacetic acid ethyl ester using immobilized ester hydrolase or alkaline to obtain (S)-α-ethyl-2-oxo-1-pyrrolidineacetate.

2. The method for the selective resolution preparation of (S)-α-ethyl-2-oxo-1-pyrrolidineacetate according to claim 1, wherein the bacterial solution of *Methylopila* sp. is an enzyme-containing bacterial suspension containing not less than 50 wt % of wet cells, which is obtained by subjecting the *Methylopila* sp. to slant culture, seed liquid culture, inoculation fermentation and concentration steps.

3. The method for the selective resolution preparation of (S)-α-ethyl-2-oxo-1-pyrrolidineacetate according to claim 1, wherein the cell immobilization method comprises dissolving the bacterial solution of *Methylopila* sp. in a buffer solution, adding at least one adsorbent and/or cross-linking agent, and stirring and suction-filtrating the same to obtain the immobilized bacterial agent;

the adsorbent is selected from any one of diatomaceous earth or activated carbon; and the cross-linking agent is selected from any one of glutaraldehyde, toluene diisocyanate or bis-diazotized benzidine.

4. The method for the selective resolution preparation of (S)-α-ethyl-2-oxo-1-pyrrolidineacetate according to claim 3, wherein the immobilized resolution enzyme achieved in the immobilized bacterial agent using the cell immobilization method has an enzyme activity recovery of not less than 90% and an adsorption rate of not lower than 95%, and the number of reuse times of the immobilized bacterial agent is not lower than 35.

5. The method for the selective resolution preparation of (S)-α-ethyl-2-oxo-1-pyrrolidineacetate according to claim 4, wherein the cell immobilization method comprises first adding the adsorbent, then stirring and mixing uniformly, and adding the crosslinking agent.

6. The method for the selective resolution preparation of (S)-α-ethyl-2-oxo-1-pyrrolidineacetate according to claim 5, further comprising adding polyethyleneimine during the addition of the crosslinking agent.

7. The method for the selective resolution preparation of (S)-α-ethyl-2-oxo-1-pyrrolidineacetate according to claim 1, wherein the temperature of the resolution reaction is 25-37° C., and the method further comprises adding a 15-25 v/v % aqueous sodium carbonate solution dropwise to control the pH of the reaction process at 6.5-8.5, and carrying out the reaction for 2-15 h.

8. The method for the selective resolution preparation of (S)-α-ethyl-2-oxo-1-pyrrolidineacetate according to claim 7, wherein, in the resolution reaction, the mass concentration of (R,S)-α-ethyl-2-oxo-1-pyrrolidineacetic acid ethyl ester in the reaction system is 160-500 g/L.

9. The method for the selective resolution preparation of (S)-α-ethyl-2-oxo-1-pyrrolidineacetate according to claim 8, wherein the immobilized bacterial agent has a dosage concentration of 5-25 g/L on a wet weight basis in the reaction system.

10. The method for the selective resolution preparation of (S)-α-ethyl-2-oxo-1-pyrrolidineacetate according to claim 9, wherein the enantiomeric excess value $e.e._s$ (%) is not less than 99.5 and the conversion rate is not lower than 49%, as detected by HPLC after the completion of the resolution reaction.

11. The method for the selective resolution preparation of (S)-α-ethyl-2-oxo-1-pyrrolidineacetate according to claim 1, wherein after said step (2), (R)-α-ethyl-2-oxo-1-pyrrolidineacetic acid in the aqueous phase is recovered, and is subjected to racemization and esterification to obtain a starting substrate material.

12. The method for the selective resolution preparation of (S)-α-ethyl-2-oxo-1-pyrrolidineacetate according to claim 1, wherein, in said step (3), (S)-α-ethyl-2-oxo-1-pyrrolidineacetate is obtained by the immobilized ester hydrolase hydrolysis, and is then concentrated and crystallized to obtain a crude product thereof.

13. The method for the selective resolution preparation of (S)-α-ethyl-2-oxo-1-pyrrolidineacetate according to claim 1, wherein, in said step (3), the alkaline solution used for the alkaline hydrolysis is 200-400 g/L of an ionic membrane alkaline solution, allowing the pH value of the reaction to be not less than 13, the reaction temperature is 10-20° C. until the substrate hydrolysis reaction is completed, and then the crude product is obtained by concentration and crystallization.

* * * * *